(12) United States Patent
Zhang et al.

(10) Patent No.: US 11,541,356 B2
(45) Date of Patent: Jan. 3, 2023

(54) SYSTEMS FOR UTILIZING CROSSFLOW FILTRATION FOR CELL ENRICHMENT

(71) Applicant: Global Life Sciences Solutions USA LLC, Marlborough, MA (US)

(72) Inventors: Chengkun Zhang, Niskayuna, NY (US); Kashan A. Shaikh, Niskayuna, NY (US); Weston B. Griffin, Niskayuna, NY (US); Reginald Donovan Smith, Niskayuna, NY (US)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 141 days.

(21) Appl. No.: 16/753,026

(22) PCT Filed: Oct. 3, 2018

(86) PCT No.: PCT/EP2018/076930
§ 371 (c)(1),
(2) Date: Apr. 2, 2020

(87) PCT Pub. No.: WO2019/068776
PCT Pub. Date: Apr. 11, 2019

(65) Prior Publication Data
US 2020/0231921 A1 Jul. 23, 2020

(51) Int. Cl.
*B01D 63/08* (2006.01)
*B01D 61/14* (2006.01)
(Continued)

(52) U.S. Cl.
CPC ............. *B01D 63/082* (2013.01); *A61M 1/34* (2013.01); *A61M 1/3482* (2014.02);
(Continued)

(58) Field of Classification Search
CPC .... B01D 63/08; B01D 63/082; B01D 63/087; B01D 69/02; B01D 69/10; B01D 61/147;
(Continued)

(56) References Cited

U.S. PATENT DOCUMENTS 3,342,729 A    9/1967   Strand
4,375,415 A *   3/1983   Lavender ............... B01D 65/08
                                                                210/651

(Continued)

FOREIGN PATENT DOCUMENTS

JP     2013513406 A    4/2013
JP     2014521333 A    8/2014
WO   2013019154 A1   2/2013

OTHER PUBLICATIONS

PCT International Search Report and Written Opinion for PCT Application No. PCT/EP2018/076930 dated Mar. 22, 2019 (14 pages).

(Continued)

*Primary Examiner* — John Kim
(74) *Attorney, Agent, or Firm* — Eversheds Sutherland (US) LLP

(57) ABSTRACT

A disposable cell enrichment kit includes a crossflow filtration device configured to be disposed along a main loop pathway and to receive a process volume containing a biological sample and utilize crossflow filtration, via a micro-porous membrane, to retain a specific cell population in a retentate from the process volume and to remove a permeate including certain biological components from the process volume. The crossflow filtration device includes a laminated filtration unit that includes the micro-porous membrane, a first mating portion, a second mating portion, and a membrane support. The membrane support includes a first plurality of structural features that define a first plurality of openings, wherein the first plurality of structural features (Continued)

are coupled to the micro-porous membrane and provide support to the micro-porous membrane, and the first plurality of openings allow the permeate to flow through them after crossing the micro-porous membrane.

14 Claims, 12 Drawing Sheets

(51) Int. Cl.
```
B01D 69/02    (2006.01)
B01D 69/10    (2006.01)
B01D 61/18    (2006.01)
C12M 3/06     (2006.01)
A61M 1/34     (2006.01)
C12M 1/00     (2006.01)
C12M 1/26     (2006.01)
B01D 25/21    (2006.01)
```
(52) U.S. Cl.
CPC ......... *B01D 25/215* (2013.01); *B01D 61/147* (2013.01); *B01D 61/18* (2013.01); *B01D 63/08* (2013.01); *B01D 63/087* (2013.01); *B01D 69/02* (2013.01); *B01D 69/10* (2013.01); *C12M 3/06* (2013.01); *C12M 29/04* (2013.01); *C12M 33/14* (2013.01); *C12M 47/02* (2013.01); *A61M 2205/3331* (2013.01); *A61M 2205/3379* (2013.01); *B01D 2313/086* (2013.01); *B01D 2313/10* (2013.01); *B01D 2313/12* (2013.01); *B01D 2313/14* (2013.01); *B01D 2313/143* (2013.01); *B01D 2313/146* (2013.01); *B01D 2313/21* (2013.01); *B01D 2313/58* (2013.01); *B01D 2315/10* (2013.01); *B01D 2315/16* (2013.01); *B01D 2325/04* (2013.01)

(58) Field of Classification Search
CPC ................ B01D 61/18; B01D 25/215; B01D 2313/086; B01D 2313/10; B01D 2313/12; B01D 2313/14; B01D 2313/143; B01D 2313/146; B01D 2313/21; B01D 2313/58; B01D 2315/10; B01D 2315/16; B01D 2325/04; C12M 29/04; C12M 33/14; C12M 47/02; C12M 3/06; A61M 1/34; A61M 1/3482; A61M 2205/3379; A61M 2205/3331
See application file for complete search history.

(56) References Cited

U.S. PATENT DOCUMENTS

| | | |
|---|---|---|
| 4,411,792 A | 10/1983 | Babb |
| 4,735,718 A | 4/1988 | Peters |
| 4,846,970 A | 7/1989 | Bertelsen et al. |
| 4,882,050 A | 11/1989 | Kopf |
| 5,034,124 A | 7/1991 | Kopf |
| 5,342,517 A | 8/1994 | Kopf |
| 5,868,930 A | 2/1999 | Kopf |
| 7,316,780 B1 * | 1/2008 | Fendya .................. B01D 61/22 210/504 |
| 8,007,670 B2 | 8/2011 | Connors, Jr. |
| 11,027,239 B2 * | 6/2021 | Zhang ................. A61M 1/3482 |
| 2002/0033367 A1 | 3/2002 | Prince et al. |
| 2007/0056894 A1 * | 3/2007 | Connors, Jr. ........ B01D 63/082 210/321.75 |
| 2011/0139723 A1 | 6/2011 | Griffin et al. |
| 2011/0189150 A1 | 8/2011 | Bosch et al. |
| 2012/0125847 A1 | 5/2012 | Sehgal |
| 2012/0134974 A1 | 5/2012 | Sehgal |
| 2013/0029411 A1 * | 1/2013 | Roy ....................... C12M 47/02 435/325 |
| 2015/0093739 A1 | 4/2015 | Wood et al. |
| 2015/0164949 A1 | 6/2015 | Sowemimo et al. |
| 2016/0106353 A1 | 4/2016 | Schuetz et al. |

OTHER PUBLICATIONS

Non-Final Office Action for U.S. Appl. No. 15/726,013 dated Dec. 3, 2019 (15 pages).

Chiu, et al., "Enhancement of Microfluidic Particle Separation Using Cross-Flow Filters with Hydrodynamic Focusing", Biomicrofluidics, https://www.ncbi.nlm.nih.gov/pmc/articles/PMC4723399/, 2016, 10(1):13 pages.

Swargaloganathan "Development of a Cross Flow Filtration Device for Human Blood Cell Fractionation", 40th Annual Northeast Bioengineering Conference (NEBEC), http://ieeexplore.ieee.org/document/6972952/, Apr. 25-27, 2014.

Vandelinder, et al., "Separation of Plasma from Whole Human Blood in a Continuous Cross-Flow in a Molded Microfluidic Device", American Chemical Society, http://pubs.acs.org/doi/abs/10.1021/ac060042r, Apr. 26, e006.

JP Office Action for Japanese Application No. 2020-519357, dated Aug. 12, 2022, English Translation, 11 pages.

* cited by examiner

SYSTEMS FOR UTILIZING CROSSFLOW FILTRATION FOR CELL ENRICHMENT

CROSS REFERENCE TO RELATED APPLICATIONS

This application claims the priority benefit of PCT/EP2018/076930 filed on Oct. 3, 2018, which claims priority to U.S. patent application Ser. No. 15/726,013 filed Oct. 5, 2017, the entire contents of which are hereby incorporated by reference herein.

BACKGROUND

The subject matter disclosed herein relates to systems and methods for utilizing crossflow filtration for cell enrichment.

In cellular immunotherapies (e.g., autologous cellular immunotherapies), a patient's own blood, fluid, tissue, or cell sample is collected and a cellular therapy is generated from or based on the collected sample. The cellular therapy product is delivered back into the patient. For example, apheresis may be isolated from the patient and a desired cell population (e.g., white blood cells) enriched for or separated from the collected blood for manufacturing the cellular therapy. Typically, cell enrichment includes separation techniques (e.g., centrifugation-based techniques) that are costly, manual labor intensive, time-consuming, and complex.

BRIEF DESCRIPTION

Certain embodiments commensurate in scope with the originally claimed subject matter are summarized below. These embodiments are not intended to limit the scope of the claimed subject matter, but rather these embodiments are intended only to provide a summary of possible forms of the present disclosure. Indeed, the disclosed techniques may encompass a variety of forms that may be similar to or different from the embodiments set forth below.

In accordance with a first embodiment, a filtration device for a disposable cell enrichment kit is provided. The filtration device includes a first mating portion, a second mating portion, at least one inlet port, and at least one outlet port. The filtration device also includes a micro-porous membrane disposed between the first and second mating portions, wherein the micro-porous membrane and either the first mating portion or the second mating portion together define at least a portion of a single channel configured to receive a process volume containing a biological sample, and the single channel extends parallel to the micro-porous membrane. The filtration device further includes a membrane support disposed between the second mating portion and the micro-porous membrane, the membrane support comprising a first plurality of structural features that define a first plurality of openings, wherein the membrane support is coupled to both the second mating portion and the micro-porous membrane, and the membrane support is coupled to the micro-porous membrane via the first plurality of structural features to provide support. The second mating portion includes a second plurality of openings defined by a second plurality of structural features, wherein the second plurality of openings are configured to receive a permeate containing specific biological components that has crossed the micro-porous membrane and through the first plurality of openings of the membrane support for discharge from the filtration device, and the filtration device is configured to retain a specific cell population in a retentate from the process volume and to discharge the retentate from the at least one outlet port.

In accordance with a second embodiment, a disposable cell enrichment kit is provided. The disposable cell enrichment kit includes a crossflow filtration device configured to be disposed along a main loop pathway and configured to receive a process volume containing a biological sample and utilize crossflow filtration, via a micro-porous membrane, to retain a specific cell population in a retentate from the process volume and to remove a permeate including certain biological components from the process volume. The crossflow filtration device includes a laminated filtration unit. The laminated filtration unit includes the micro-porous membrane, a first mating portion, a second mating portion, and a membrane support. The membrane support includes a first plurality of structural features that define a first plurality of openings, wherein the first plurality of structural features are coupled to the micro-porous membrane and provide support to the micro-porous membrane, and the first plurality of openings allow the permeate to flow through them after crossing the micro-porous membrane. The membrane support is configured to be disposed between the micro-porous membrane and either the first mating portion or the second mating portion.

In accordance with a third embodiment, a system is provided. The system includes a disposable cell enrichment kit configured to be coupled to a fluid management system. The kit includes a crossflow filtration device disposed along a main loop pathway and configured to receive a process volume containing a biological sample and to utilize crossflow filtration, via a micro-porous membrane, to retain a specific cell population from the process volume and to remove a permeate including certain biological components from the process volume. The kit also includes a process vessel disposed along the main loop pathway downstream of the crossflow filtration device and configured to receive the process volume following from crossflow filtration via the crossflow filtration device. The kit further includes a buffer vessel disposed along a buffer pathway coupled to the main loop pathway and configured to provide a buffer to the process volume. The system also includes the fluid management system. The fluid management system includes a waste pump coupled to the crossflow filtration device via a waste pathway and configured to discharge the permeate from the crossflow filtration device via the waste pathway at a controlled rate. The fluid management system also includes a buffer pump disposed along the main loop pathway to maintain flow of the buffer to the process volume at a controlled rate. The fluid management system further includes a main loop pump disposed along the main loop pathway to maintain flow of the process volume into and out of the crossflow filtration device. The fluid management system and the disposable cell enrichment kit, in operation, automatically enrich the specific cell population from the biological sample by maintaining the process volume at a specific volume range within the process vessel during washing of the retentate by providing the buffer to the process volume.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
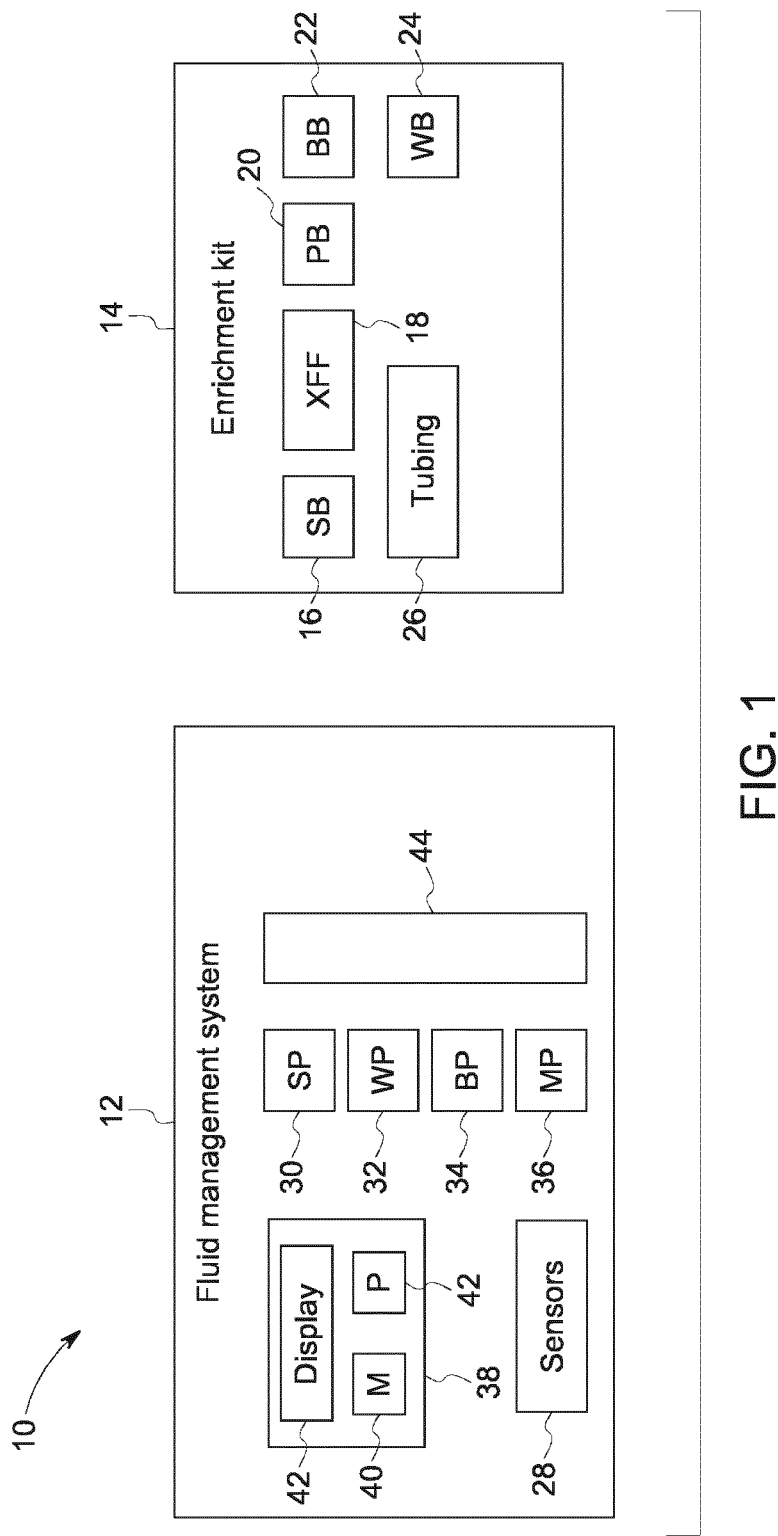
FIG. 1 is a schematic diagram of an embodiment of a system for enriching a desired cell population.

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time-consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

Disclosed herein are systems and methods for enriching a desired cell population (e.g., white blood cells) from a biological sample (e.g., blood, tissue, etc.) for manufacturing cellular immunotherapies. The disclosed embodiments include a disposable cell enrichment kit configured to be coupled to a fluid management system to form an automated, scalable and closed system for enriching the desired cell population. The disposable cell enrichment kit may include a source bag or vessel (e.g., for introducing the biological sample into the kit), a crossflow filtration device (e.g., to separate the desired cell population from the biological sample), process bag or vessel to serve as a reservoir to feed or supply a process volume to the crossflow filtration device, a buffer bag or vessel (e.g., to provide a buffer to the process volume to maintain a desired volume during washing and to provide the fluid necessary for washing), and a waste bag or vessel to collect a permeate containing undesired biological components (e.g., plasma, platelets, etc.) from the crossflow filtration device. The fluid management system includes pumps coupled to various pathways of the cell enrichment kit to maintain fluid flow along these pathways (e.g., buffer, process volume, waste, etc.). The crossflow filtration device includes a top portion, a bottom portion, and a membrane (e.g., micro-porous membrane such as a track-etched membrane) disposed between the top and bottom portions. It should be noted that upper and lower portion are not limiting with respect to direction of gravity. The device can be oriented in any position (with or without gravity). The terms upper and lower are simply for convenience in referencing the drawings. The membrane may include substantially uniform pore size with a tight tolerance. A channel (e.g., single channel) is defined between the membrane and bottom portion. The channel receives the process volume at a flow rate that generates a shear that separates the undesired biological components (e.g., permeate), via the membrane, from the process volume. A certain shear rate (i.e., rate of change of velocity over a given change in distance) is necessary to provide momentum for the cells of interest to move along the fluid, while reducing the chances of the cells of interest from crossing the membrane into the waste pathway. The shear rate (e.g., approximately 5000 $s^{-1}$) generated in the channel is designed to keep the cells of interest moving along the passage and away from the wall. Smaller particles (e.g., undesired biological components) may be less effected by the shear and may more easily pass through the membrane to the waste pathway. The remaining process volume (e.g., retentate) is recirculated back to the process bag. Recirculation enables a volume to pass across the membrane multiple times (e.g., enabling a smaller membrane), while enabling constant adjustment of the volume (e.g., to keep the density of the cells of interest the same during the process). In certain embodiments, the permeate is discharged from the crossflow filtration device at a controlled rate, while buffer is provided to the process volume to maintain the process volume in the process bag at a constant volume (e.g., during washing). In certain embodiments, prior to washing, the process volume is concentrated to a desired volume. Further, after washing, the process volume may also be concentrated to a desired volume. The cell enrichment kit provides a kit that can be removably coupled to the fluid management system to so that components of the kit are aligned with components of the fluid management system (e.g., pumping tube sections of the kit to be automatically aligned with the components of the pumps of the fluid management system, align bags to load cells, align components to sensors, etc.) to simplify utilization of the kit. In addition, the integration of the membrane provides a functionally closed kit. The disclosed embodiments provide an automated system where the functionally is performed in a closed system, reducing the labor utilized in cell enrichment.

FIG. 1 is a schematic diagram of an embodiment of a system 10 for enriching a desired cell population. The system 10 may be utilized for enriching a desired cell type (e.g., white blood cells) within a biological sample (e.g., blood, tissue, etc.) for manufacturing cell immunotherapies by separating undesired biological components (e.g., plasma, platelets, red blood cells, etc.) from the biological sample. Although the system 10 is described as being used for cell enrichment, it can be utilized for other bioprocessing applications (e.g., enriching for certain size and/or types of proteins). The system 10 may also be useful or other types of crossflow filtration applications where smaller/more deformable particles are removed from a solution while retaining larger/more rigid particles.

The system 10 includes a fluid management system 12 and an enrichment kit 14 (e.g., disposable cell enrichment kit). The entire kit 14 is disposable. The enrichment kit 14 includes a source bag 16, a crossflow filtration device 18, a process bag 20, a buffer bag 22, and a waste bag 24 coupled together via various pathways. Although 16, 20, 22, and 24 are described as bags, they may be any type of container or receptacle or vessel. The various components of the kit 14 are coupled together and/or to components of the fluid management system 12 (e.g., pumps, pinch valves, etc.) via tubing 26. In addition, valves may be disposed throughout the kit. In addition, in certain embodiments, certain components of the kit 14 may be coupled to sensors 28 to provide feedback to the fluid management system 12. The sensors 28, as depicted, may be part of the system 12 to reduce the costs of the kit 14. In certain embodiments, the kit 14 may include some sensors 28 (e.g., disposable sensors). For example, the process bag 20 may be coupled to a load cell sensor that measures the weight of process volume within the bag 20. In some embodiments, flow sensors may be disposed within the tubing 26 upstream and downstream of certain components (e.g., crossflow filtration device 18) of the kit 14 to measure the flow rate into or out of the components. In some other embodiments, pressure transducers may be disposed within the tubing 26 upstream and downstream of certain components (e.g., crossflow filtration device 18), and in the waste line to measure trans-membrane pressure or detect membrane fouling. The sensors 28 may include sensors that interacts with the fluids within the kit 14 without contacting the fluid (e.g., optical sensors, ultrasound sensors, etc.). In certain embodiments, a portion of a sensor (e.g., chemoptical sensor) may be associated with the kit 14, while the other portion (e.g., hardware) is associated with the system 12.

The source bag 16 (e.g., disposed along a source pathway) is configured to receive the biological sample and to provide the process volume with the biological sample to the rest of the kit 14 (e.g., crossflow filtration device 18). The crossflow filtration device 18 (e.g., disposed along a main loop pathway) is a membrane-based device for separating undesired biological products (e.g., plasma, platelets, red blood cells, etc.) from the biological sample in the process volume). The process volume is circulated through the crossflow filtration device 18 at a high enough flow rate to generate a required shear rate within a single channel formed within the device 18 adjacent the membrane. In certain embodiments, the membrane is part of a laminated structure. The structure of the crossflow filtration device 18 is described in greater detail below. The process bag 20 (e.g., disposed along the main loop pathway) is configured to receive the process volume (e.g., retentate) after crossflow filtration by the crossflow filtration device 18 and/or buffer from the buffer bag 22.

The process bag 20 is designed to promote mixing within the bag 20. For example, the process bag 20 includes a first port 21 (e.g., an inlet) to receive the process volume and a second port 22 (e.g., an outlet) to discharge the process volume into the main loop pathway, where the inlet is located at the bottom of the bag 20. In certain embodiments, the process bag 20 tapers from the first port 21 to the second port 22 (e.g., forming a conical shape). In certain embodiments, the first port 21 of the process bag 20 is angled relative to the second port 22 to generate a vortex (e.g., counter-clockwise vortex) within the bag 20. The tapered or conical portion of the process bag 20 encourages mixing (e.g., to keep cells from settling) to ensure that a desired wash factor (e.g., for plasma) is achieved in a given amount of time.

The buffer bag 22 (e.g., disposed along a buffer pathway coupled to the main loop pathway) is configured to receive and provide buffer to the process volume. The buffer is provided at a location upstream of the crossflow filtration device 18, between the crossflow filtration device 18 and the process bag 20, or at the process bag 20. During washing of the retentate or process volume, the buffer bag 22 provides buffer to the process volume to maintain the process volume at a constant desired volume. The waste bag 24 (e.g., disposed along a waste pathway) is configured to receive the permeate (e.g., containing the undesired biological products) from the crossflow filtration device 18.

The fluid management system 12 includes a source pump 30, a waste pump 32, a buffer pump 34, and a main loop pump 36. The source pump 30 is configured to couple to the source pathway and to introduce flow of the biological sample into the process volume from the source bag 16). The waste pump 32 is configured to couple to the waste pathway to regulate flow of the permeate from the crossflow filtration device 18 to the waste bag 24. The buffer pump 34 is configured to couple to the buffer pathway to regulate flow of the buffer from the buffer bag 22 to the process bag 20 or a location along the main loop pathway to be provided to the processing volume (e.g., to maintain a constant volume during the washing step). The main loop pump 36 is configured to couple to the main loop pathway to maintain flow of the process volume from the process bag 20 to the crossflow filtration device 18 and from the device 18 back to the process bag 20.

The fluid management system 12 also includes a computing device 38. The computing device 38 controls the system 10 to enable a fully automated system for cell enrichment. The computing device 38 includes a memory 40 and a processor 42 to execute code or instructions stored within the memory 40. The computing device 38 also includes a display 42 to display pressure readings, flow rates, status of the system, current point in the process, and other system parameters relevant to the cell enrichment process. The instructions stored on the memory 40 may be encoded in programs or codes stored in a tangible non-transitory computer-readable medium. The memory 40 may include a computer readable medium, such as, without limitation, a hard disk drive, a solid state drive, diskette, flash drive, a compact disc, a digital video disc, random access memory (RAM), and/or any suitable storage device that enables the processor 42 to store, retrieve, and/or execute instructions and/or data. The processor 42 may be a general purpose processor (e.g., processor of a desktop/ laptop computer), system-on-chip (SoC) device, or application-specific integrated circuit, or some other processor configuration. The processor 42 may execute instructions to receive input from sensors (e.g., from the load cell sensor coupled to the process bag 20, flow rate sensors, etc.). The processor 42 may regulate the pumps, valves, and flow of fluids (e.g., process volume, permeate, buffer, etc.) along the various pathways of the kit 14. In certain embodiments, the processor 42 may regulate these components based on the feedback from the sensors. For example, the processor 42 may regulate these components to initially concentrate the volume of the process volume (e.g., having the biological sample) to a desired volume (e.g., 50 mL). In certain embodiments, the processor 42, subsequent to the concentration step (e.g., during a washing step), may cause the permeate to be removed from the crossflow filtration device 18 at a controlled rate, while causing buffer to be provided via the buffer bag 22 at nearly the same rate to the processing volume to maintain desired processing volume at a constant volume. In certain embodiments, the processor 42 may execute the cell enrichment process for a set time (e.g. empirically determined) to achieve a specific reduction or washing factor (e.g., 1 log or 90% residual reduction, 2 log or 99% residual reduction, etc.) in undesired biological products (e.g., platelets, plasma, red blood cells, etc.). In certain embodiments, the processor 42 may execute the cell enrichment process for a set number of cycles (e.g., passages through main loop pathway). In certain other embodiments, the processor 42 may execute the cell enrichment process in batch mode (e.g., process source volumes batch by batch).

In certain embodiments, the fluid management system 12 includes a removable receptacle or structure 44 configured to receive a portion of the kit 14. For example, the crossflow filtration device 18 may be removably inserted into the receptacle 44. Insertion of the portion of the kit 14 into the receptacle 44 enables the pumping tube sections (e.g., tubing 26, valves, etc.) to be automatically aligned with components of the pumps 30, 32, 34, 36. In certain embodiments, the system 12 may also include pinch valves and/or stopcock drives that can be coupled with the tubing or stopcocks of the kit 14.

Figure 2:
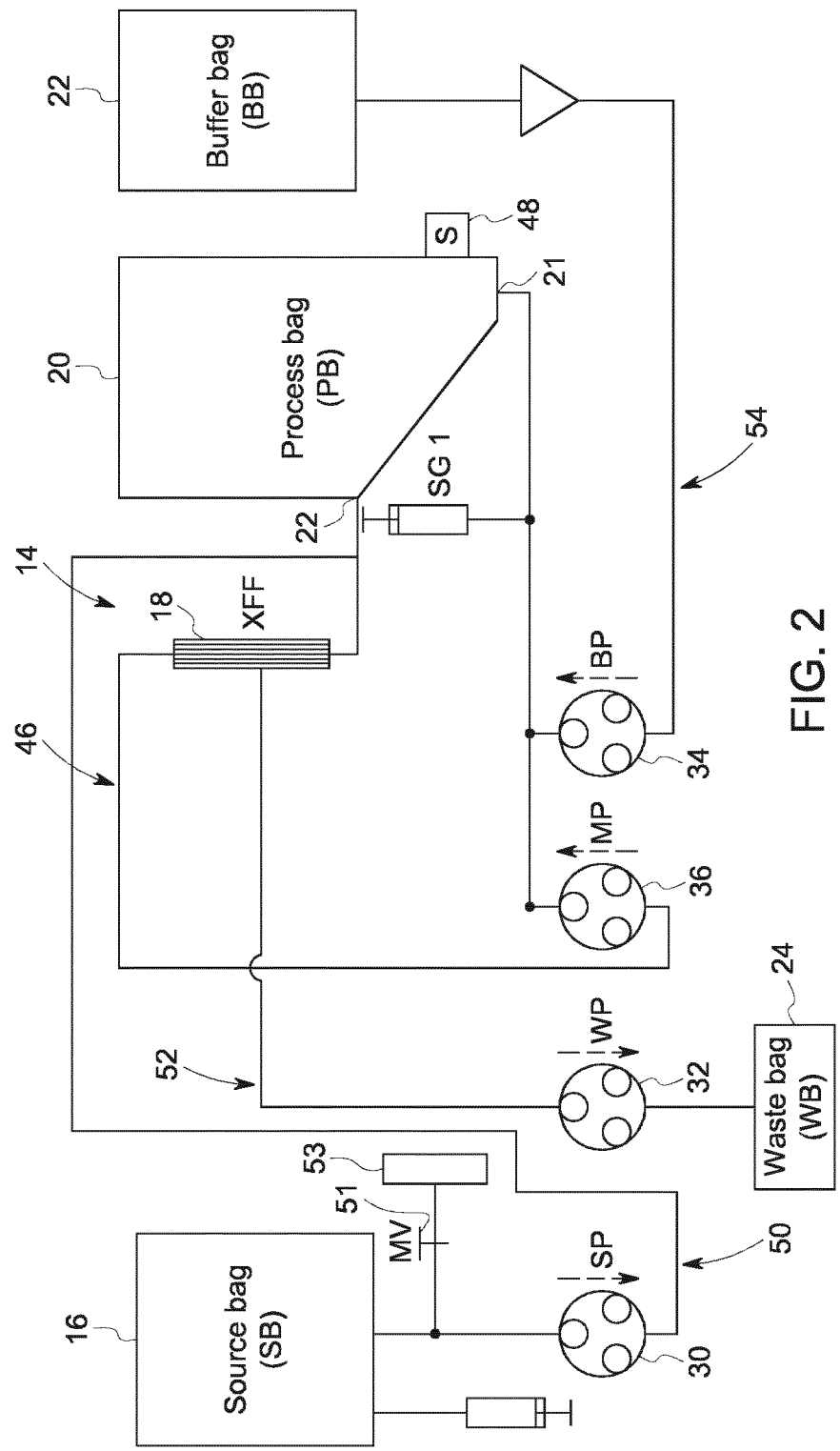
FIG. 2 is a schematic diagram of an embodiment of a flow path of an enrichment kit.

FIG. 2 is a schematic diagram of an embodiment of a flow path of the enrichment kit 14 (e.g., coupled to portions of the fluid management system 12). As depicted, the crossflow filtration device 18 and the process bag 20 are disposed along a main loop pathway 46 that circulates the process volume (including buffer) from the process bag 20 to the crossflow filtration device 18 and from the device 18 to the process bag 20. The main loop pump 36 is coupled to and/or disposed along the main loop pathway 46. The process bag 20 is located downstream of the crossflow filtration device 18 along the main loop pathway 46. The process bag 20 is coupled to a sensor 48 (e.g., load cell sensor) that helps determine the process volume in the process bag 20.

The source bag 16 is disposed along and/or coupled to a source pathway 50. The source pathway 50 provides the biological sample received at the source bag 16 (as part of the process volume) to the main loop pathway 46. As depicted, the source pathway 50 provides the biological sample to the main loop pathway 46 between both the crossflow filtration device 18 and the process bag 20 to enable better mixing in the process bag 20. In certain embodiments, the source pathway 50 provides the biological sample directly to the process bag 20 or provides the biological sample to other locations along the main loop pathway 46. The source pump 30 is coupled to and/or disposed along the source pathway 50. A valve 51 (e.g., manual valve) may be disposed along the source pathway 50 downstream of the source bag 16. The valve 51 may be closed after the biological sample is introduced along the pathway 50. In certain embodiments, the valve 51 may be opened to introduce filtered air 53 into the kit 14 to purge the line.

The crossflow filtration device 18 is coupled to a waste pathway 52 that diverts the permeate or waste containing the undesired biological products (e.g., platelets, plasma, red blood cells, etc.) isolated from the process volume away from the crossflow filtration device 18. The waste pump 32 is coupled to and/or disposed along the waste pathway 52. The waste bag 24 may be coupled to a downstream end of the waste pathway 52 to receive the permeate or waste.

The buffer bag 22 is coupled to and/or disposed along a buffer pathway 54. The buffer pathway 54 provides buffer (e.g., crossflow filtration solution) from the buffer bag 22 to a point along the main loop pathway 46 to maintain a constant volume of the process volume during washing (i.e., removal of undesired biological products via permeate). The buffer pathway 54 may be coupled to the main loop pathway 46 upstream of the crossflow filtration device 18, between the crossflow filtration device 18 and the process bag 20, or at the process bag 20. The buffer may include an osmotic solution (e.g., sodium chloride containing solution, phosphate buffered saline, lactated Ringer's solution, lactated Ringer's solution with glucose), oncotic agents, a crystalloid agents, carbohydrates, electrolytes, and/or biological buffers (e.g., HEPES, TES, EPPS, MOPS, THAM, TRIS, etc.). In certain embodiments, buffer may be added to the source material as a diluent (i.e., to perform linear dilution) prior to any processing within the system 10. In other embodiments, buffer or diluent may be added after a concentration step or after a washing step to achieve a desired cell density. In operation, the biological sample (e.g., blood from apheresis) is provided to the source bag 16 where it flows (e.g., as part of the process volume) along the source pathway 50, via the source pump 30, to the main loop pathway 46. At the main loop pathway 46, the process volume flows through the crossflow filtration device 18, where tangential or crossflow filtration occurs. In certain embodiments, the sample may be introduced, via the source pathway 50, directly to the process bag 20. Upon providing the source to the process bag 20 and/or main loop pathway 46. In particular, the crossflow filtration device 18 includes a membrane (e.g., micro-porous membrane such as track-etched membrane) having pores. The pores of the membrane may range in diameter from approximately 1 to 10 μm. In preferred embodiments, the pores may be approximately 1 μm. In other preferred embodiments, the pores may range in diameter from approximately 1.5 to 3 μm. The membrane may include an area of at least 40 $cm^2$. The process volume is circulated, via the main loop pump 36, as a laminar flow with a specific shear rate into a thin channel that interfaces with the membrane so that the undesired biological products (e.g., platelets, plasma, red blood cells, etc.) pass from the channel through the membrane as a permeate. The permeate is removed from the crossflow filtration device 18 (e.g., at a controlled rate) along the waste pathway 52. Utilizing a controlled rate that keeps the permeate rate below a natural flux rate of the membrane minimizes the occurrence of fouling the membrane. In certain embodiments, the permeate rate may be adaptively controlled. For example, a relatively smaller permeate rate may be utilized in the initiation phase of washing, then the permeate rate may be gradually increased based on empirical data or waste line pressure info. By doing so, the washing efficiency may be significantly improved.

The remaining process volume (e.g., retentate) including the desired cell population (e.g., white blood cells) flows from the crossflow filtration device 18 along the main loop pathway 46 back to the process bag 20, where the process volume is then circulated back along the main loop pathway 46 to the crossflow filtration device 18 and, subsequently, to the process bag 20 again. In certain embodiments, initially the process volume (i.e., retentate) may be concentrated by circulating the process volume through the main loop pathway 46 so that the permeate is pulled from the crossflow filtration device 18 at a controlled rate until the process volume reaches a desired or set volume (e.g., 50 mL). Upon reaching the desired or set volume, during a washing, buffer is introduced at a rate substantially the same as the controlled rate (e.g., permeate rate) that the permeate is removed from the process volume to maintain the process volume at the constant desired volume. During the washing step, the process volume (i.e., retentate) may be circulated through the main loop pathway 46 for a certain time (e.g., processing time) that has been empirically determined or modelled to achieve a particular log reduction (e.g., 1 log or 2 log) of the undesired biological products.

In certain embodiments, the system 10 maintains a permeate ratio (e.g., permeate flow rate/main loop flow rate) between approximately 1 and 3 percent through the main loop pathway 46. The permeate flow rate is the rate at which permeate is removed from the crossflow filtration device 18, while the main loop flow rate is the flow rate of the process volume through the main loop pathway 46. A smaller permeate rate results in a longer processing time. The permeate rate may range between 0.15 to 0.4 mL/min per cm$^2$ of filter surface area. The main loop flow rate will depend on the channel geometry and the desired shear rate and, in certain embodiments, may be less than 500 ml/minute.

Figure 3:
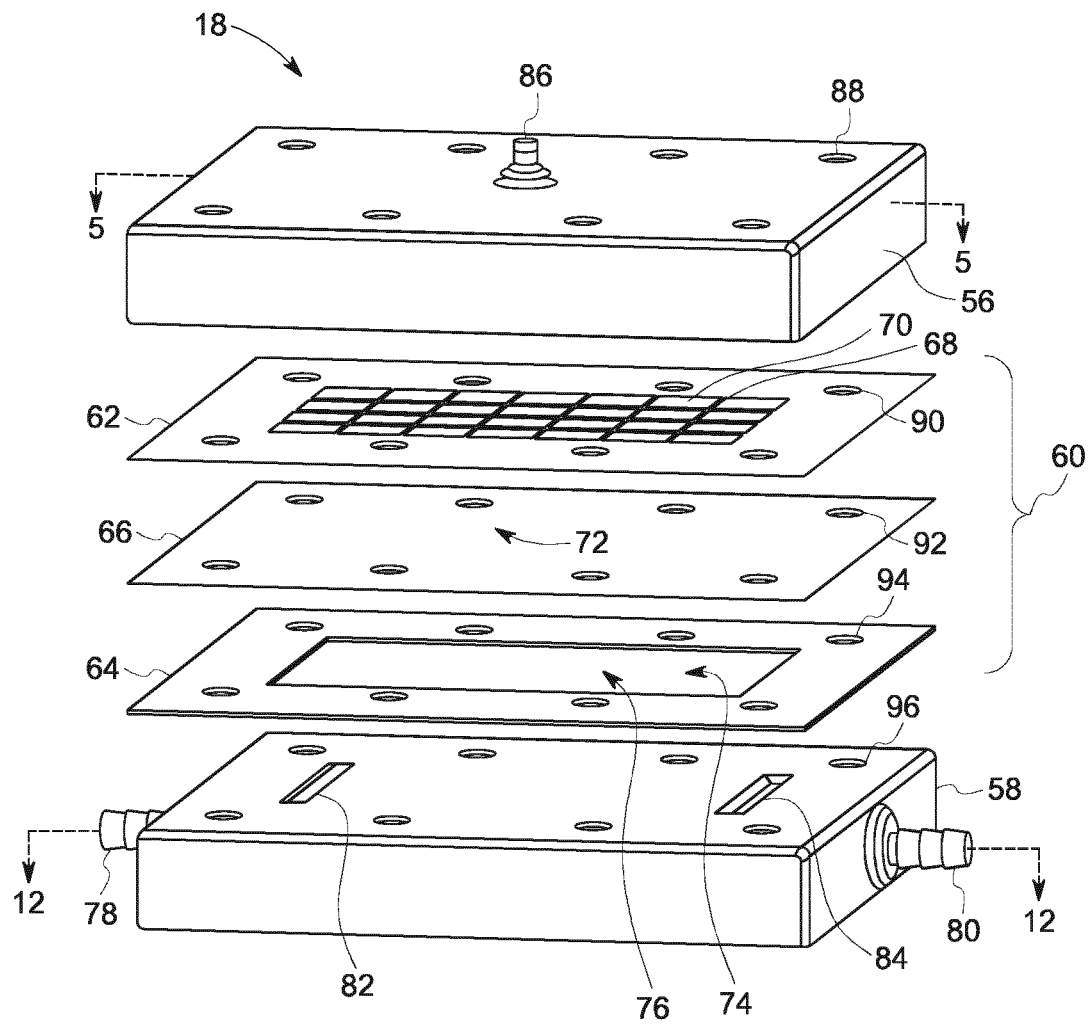
FIG. 3 is an exploded perspective view of an embodiment of a crossflow filtration device.

FIG. 3 is an exploded perspective view of an embodiment of the crossflow filtration device 18. The crossflow filtration device 18 includes a top portion or block 56, a bottom portion or block 58, and a filtration device or unit 60 (e.g., laminated filtration device) disposed between the top portion 56 and the bottom portion 58. As depicted, the filtration unit 60 includes a membrane support 62, a spacer 64 (e.g., polyimide film, or other materials with uniform thickness), and a membrane 66 (e.g., polycarbonate track-etched membrane) disposed between the membrane support 62 and the spacer 64. The components of the laminated filtration device 60 are mechanically coupled together (e.g., chemically, thermally, etc.) as described below to maintain the flatness of membrane 66 within the usable membrane area 72. In particular, the membrane support 62 helps to keep the membrane 66 from buckling or wrinkling, thus helping to maintain the flow chamber cross-sectional area over the length of the channel and, thus the shear, by keeping the membrane 66 in place. Both the membrane support 62 and the spacer 64 strengthen the membrane 66. Pressure sensitive adhesive (or other type of adhesive) may be utilized to adhere a bottom surface of the membrane 66 to a top surface of the spacer 64 and a top surface of the membrane 66 to a bottom surface of the membrane support 62.

The membrane 66 includes pores large enough to enable the undesired biological products (e.g., platelets, plasma, red blood cells, etc.) to pass through it during crossflow filtration, while not enabling the desired cell population (e.g., white blood cells) to pass through. The pores of the membrane 66 may range in diameter from approximately 1 to 10 µm. In preferred embodiments, the pores may be approximately 1 µm. In other preferred embodiments, the pores may range in diameter from approximately 1.5 to 3 µm. The membrane 66 may also include a thickness of approximately 13-25 µm.

The membrane support 62 is impermeable to liquid. The membrane support 62 include features or structural members 68 (e.g., ribs, supports, etc.) extending across a length and width of the support 60 that define openings 70 in the support 60 to enable flow (e.g., of the retentate) through the membrane 66 towards the top portion 56. The number and shape of the features 68 and openings 70 may vary. The features 68 adhere to the membrane 66 within the usable membrane area 72 (e.g., as defined by the channel) and may also be adhered to a bottom surface of the top portion 56. Adherence of usable membrane area 72 to the membrane support 62 (in particular the features 68) minimizes local membrane deflection to avoid occluding flow in the main flow channel. In addition, due to impermeability of the membrane support 62 minimizing the bondable surface area between the membrane 66 and the membrane support 62 maximizes the usable membrane area 72. A larger useable membrane area 72 enables a larger volume of sample material to be processed to achieve a desired washing factor in a given time period. In addition, these features enable the use of a single channel with a larger channel width and length. In certain embodiments, the ratio of the membrane thickness to unsupported membrane surface area may be approximately 13 µm/4×10$^9$ µm$^2$.

The spacer 64 includes an opening 74 that together with the bottom surface of the membrane 66 and the top surface of the bottom portion 58 defines a single channel 76 for the flow of the process volume through the device 18. In addition, the area within the spacer 64 defines the usual area 72 of the membrane 66. One skilled in the art will appreciate the channel length, width, and height will affect the shear rate, usable surface area, sample capacity, and processing time for a given flow rate.

The bottom portion 58 includes a feed port 78 to receive the process volume and a retentate port 80 to discharge the remaining process volume (i.e., retentate) after crossflow filtration. The bottom portion 58 includes an inlet 82 coupled to the feed port 78 that provides the process volume to the channel 76. The bottom portion 58 also includes an outlet 84 coupled to the retentate port 80 to discharge the retentate from that channel 76 and the device 18. As depicted, the inlet 82 and the outlet 84 are disposed at opposite longitudinal ends of the channel 76. The process volume has a laminar flow from the inlet 82 to the outlet 84 across the channel 76. The inlet 82 (which extends across a width of the channel 76) is configured to provide a uniform velocity across the width of the channel 76. In certain embodiments, the inlet 82 and the outlet 84 are configured to limit an amount of flow directly impinging on the membrane. In other words, the incoming flow (via the inlet 82) is directed as parallel as possible to membrane 66 the better the crossflow filtration.

The top portion 56 includes a filtrate or permeate port 86 for discharging the permeate or waste (including the undesired biological products) that was separated from the process volume from the device 18 to the waste pathway 52. The top portion 56 includes openings or ports (see FIGS. 4 and 5) defined by features or structural members (e.g., ribs, supports, etc.) that enable flow of the filtrate or permeate after crossing the membrane to the filtrate port 86 before being discharged from the device 18. The features, when matching the membrane support ribs and passage pattern, increases the area for adhesion of the membrane support to the bottom surface of the top portion and provide passages to allow the permeate to be collected in the pocket above the hole-array feature before entering the permeate port. In certain embodiments, the features of the top portion 56 may not perfectly match or align with features (e.g., ribs) of the membrane support 62. A combination of a high shear rate in the channel 76 and a low flow rate through the filtrate port 86 avoids or minimizes blocking of the pores of the membrane 66 with cells and/or particles that cannot pass through the membrane 66.

The top portion 56, the membrane support 62, the membrane 66, the spacer 64, and the bottom portion 58 all include respective openings 88, 90, 92, 94, 96. The respective openings 88, 90, 92, 94, 96 are vertically aligned with respect to each other and enable fasteners (e.g., rods, bolts, etc.) to be disposed through them to assemble the components of the crossflow filtration device 18 together.

Figure 4:
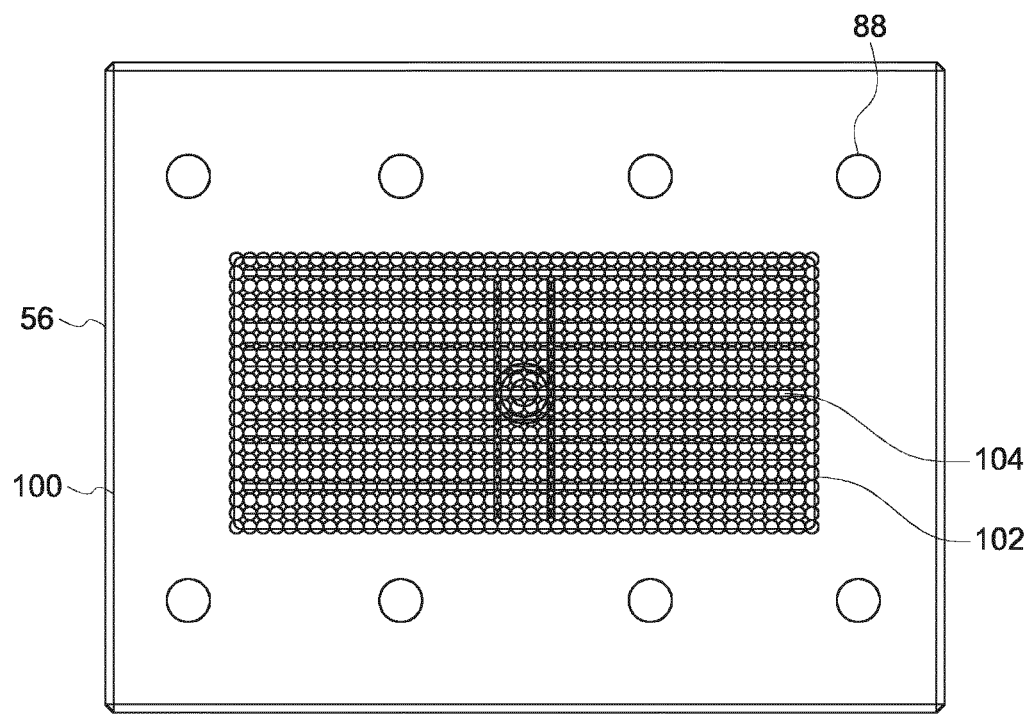
FIG. 4 is a bottom view of a top portion of the crossflow filtration device of FIG. 3.
Figure 5:
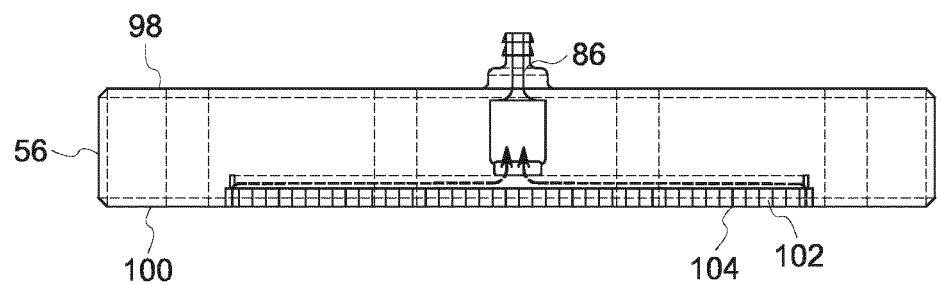
FIG. 5 is a cross-sectional view of the top portion of the crossflow filtration device of FIG. 3 taken along line 5-5.
Figure 6:
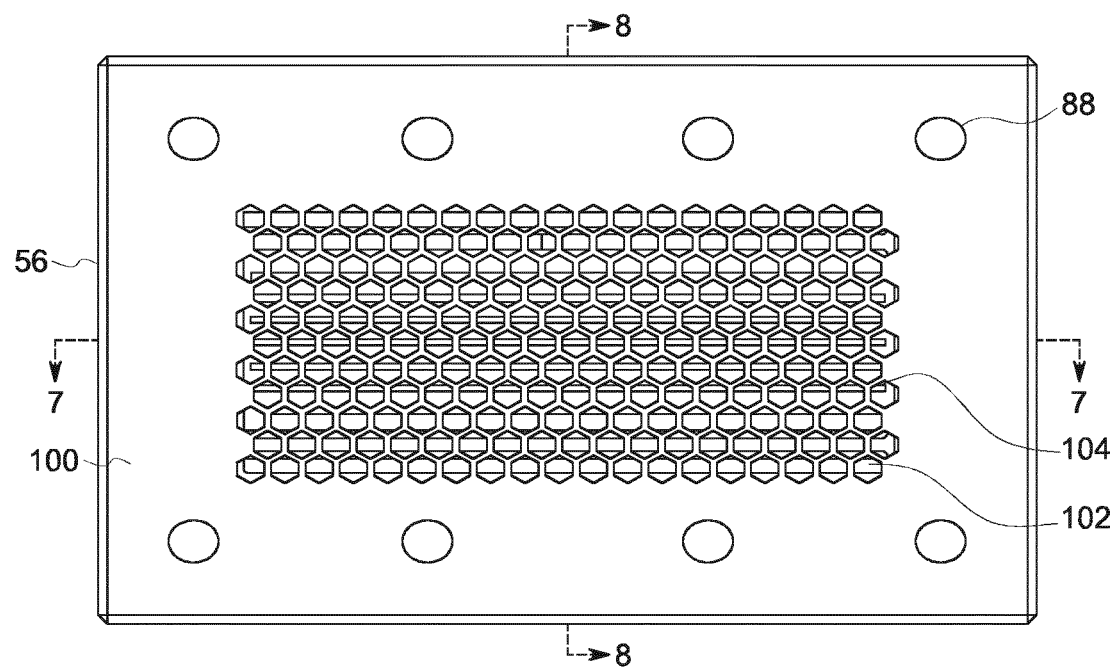
FIG. 6 is a bottom view of an embodiment of a top portion of a crossflow filtration device (e.g., having a honey comb geometry on bottom surface)
Figure 7:
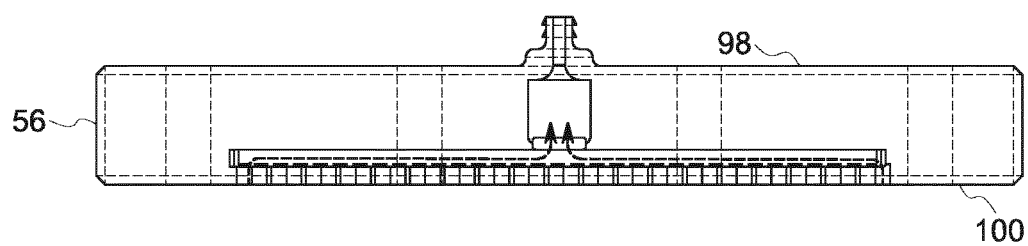
FIG. 7 is a cross-sectional view of an embodiment of the top portion of FIG. 6 taken along line 7-7.
Figure 8:
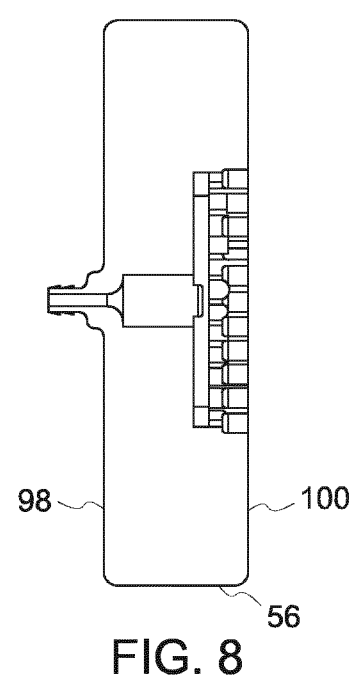
FIG. 8 is a cross-sectional view of an embodiment of the top portion of FIG. 6 taken along line 8-8.

FIGS. 4 and 5 are views of the top portion 56 of the crossflow filtration device 18 of FIG. 3. As depicted, the filtrate port 86 extends from a top surface 98 of the top portion 56. In certain embodiments, the filtrate port 86 may be disposed on a different surface (e.g., side surface) of the top portion 56. A bottom surface 100 includes openings 102, defined by features or structural supports 104 (e.g., ribs, supports, etc.), that enable flow of the filtrate or permeate after crossing the membrane to flow to the filtrate port 86 before being discharged from the device 18. The openings 102 provide a low resistance fluid path for the flow of the permeate. The shape of the openings 102 and features 104 may vary. For example, as depicted in FIGS. 4 and 5, the ports 102 and features 104 defined by an array of circular openings. And, as depicted in FIGS. 6, 7, and 8, the ports 102 and features 104 define a honeycomb structure. As shown in FIGS. 5, 7, and 8, additional channels or pathways allow fluid to flow from the openings 102 to the permeate port 86, while also providing structural support for features 104. In certain embodiments, the geometry of the features 68 of the membrane support 62 may be different from the features 104 on the bottom surface 100 of the top portion 56 (e.g., the membrane support 68 of FIG. 3, as well as an assembled filtration unit 60 of FIG. 9, and the bottom surface 100 of the top portion 56 in FIG. 4). In certain embodiments, the geometry of the features 68 of the membrane support 62 may be the same as the features 104 on the bottom surface 100 of the top portion 56 (e.g., the membrane support 68 of an assembled filtration unit 60 of FIG. 10 and the bottom surface 100 of the top portion 56 in FIG. 6 with both having the honeycomb structure).

Figure 11:
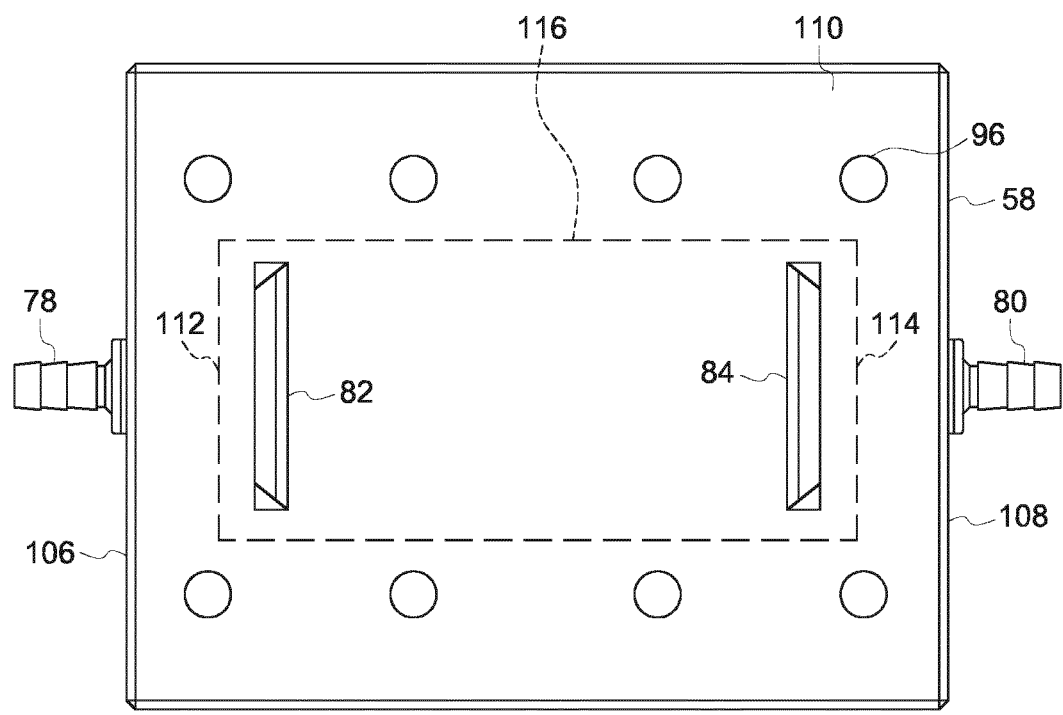
FIG. 11 is a top view of the bottom portion of the crossflow filtration device of FIG. 3.
Figure 12:
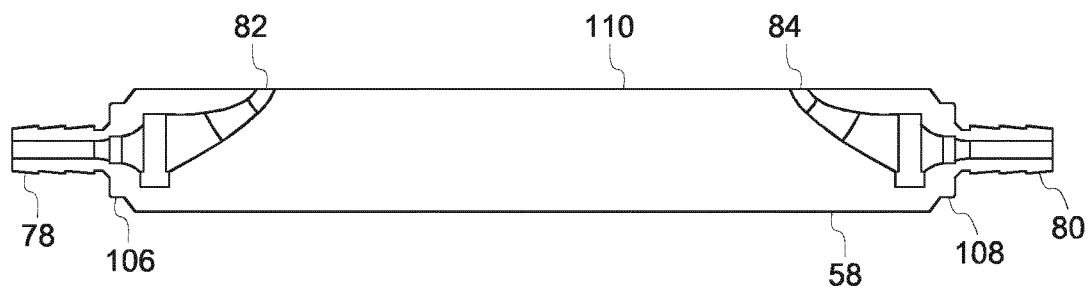
FIG. 12 is a cross-sectional view of the bottom portion of the crossflow filtration device of FIG. 3 taken along line 12-12.

FIGS. 11 and 12 are views of the bottom portion 58 of the crossflow filtration device 18 of FIG. 3. As depicted, the feed port 78 and the retentate port 80 are disposed on opposite side surfaces 106, 108, respectively, of the bottom portion 58. In some embodiments, tubing is secured to the ports via fasteners (e.g., zip ties). The inlet 82 and the outlet 84 are disposed on a top surface 110 of the bottom portion 58 adjacent opposite longitudinal ends 112, 114 of an area 116 (indicated by dashed lines) where both the channel 76 and usable membrane area 72 are located. The port 78 extends to inlet 82 and the outlet 84 extends to port 80. Both ports 78, 80 have a smooth contoured shape to enable a smoother flow of the process flow into and out of the channel 76. The contoured shape of the channel from port 78 to strip opening inlet 82 enables a thin flow stream of close to uniform flow velocity through the channel 76 and over the entire width. In certain embodiments, the bottom portion 58 may be a flat plate without features. In this embodiment, the spacer layer may define the features of the plenum (e.g., transition from a circular port to a wide flow channel. In such an embodiment, the feed and retentate ports and/or the plenums may then be located in the top block.

Figure 9:
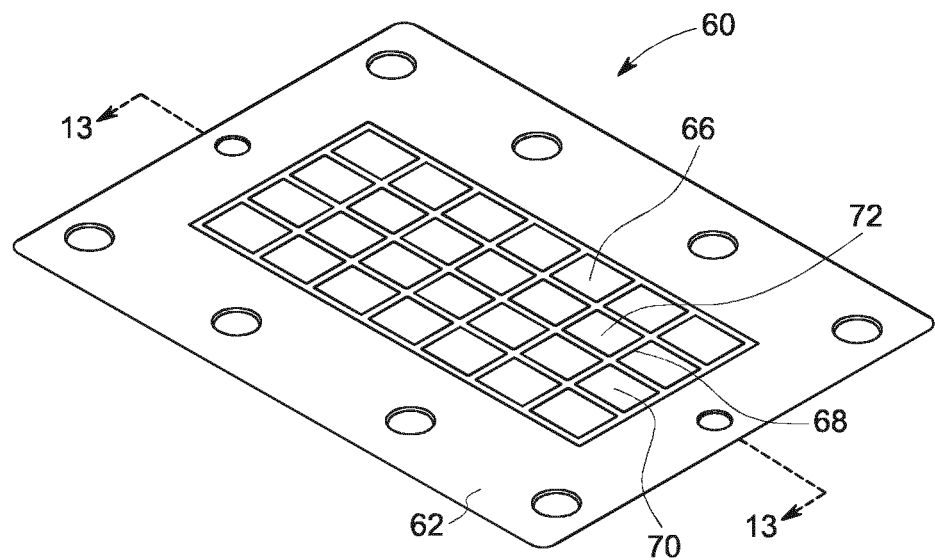
FIG. 9 is a perspective view of an embodiment of an assembled filtration unit of the crossflow filtration device of FIG. 3.
Figure 10:
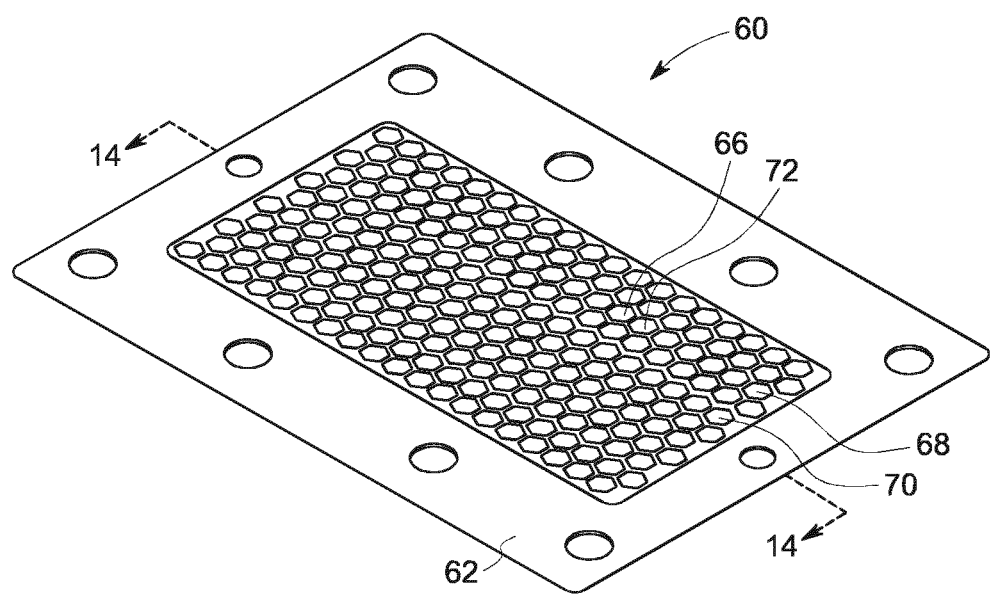
FIG. 10 is a perspective view of an embodiment of an assembled filtration unit of the crossflow filtration device having a honeycomb geometry.
Figure 13:
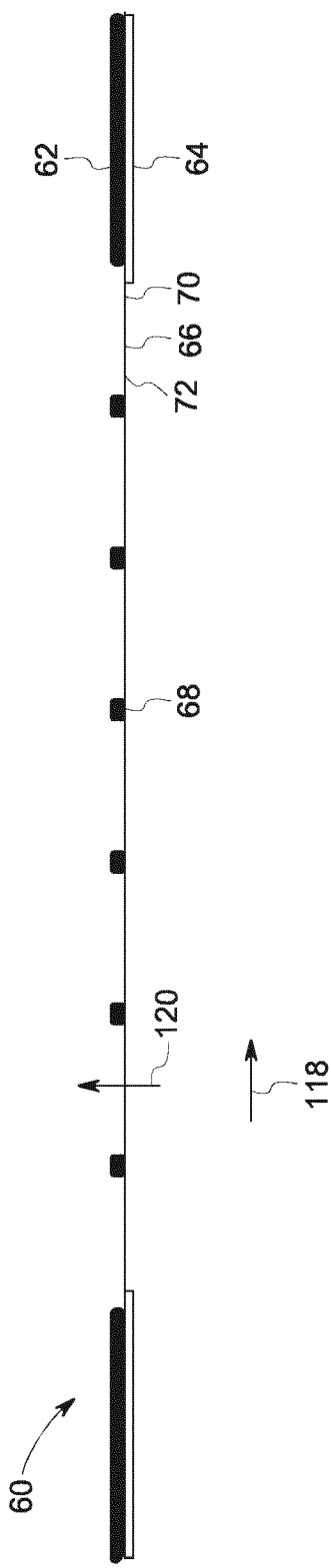
FIG. 13 is a cross-sectional view of the filtration unit of FIG. 9 taken along line 13-13.
Figure 14:
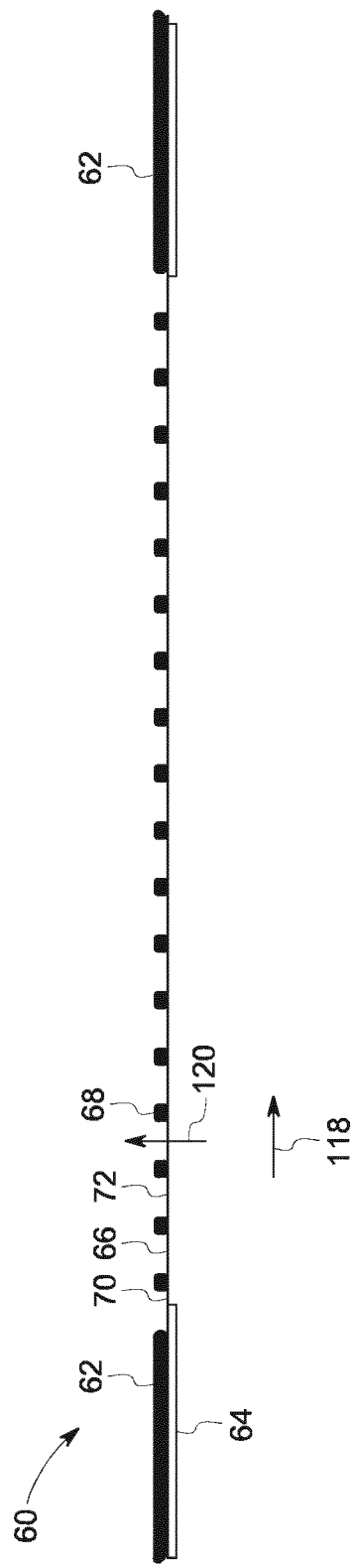
FIG. 14 is a cross-sectional view of the filtration unit of FIG. 10 taken along line 14-14.

FIGS. 13 and 14 are cross-sectional views of the assembled filtration units 60 of FIGS. 9 and 10, respectively. As described above, the process volume flows in the direction 118 from the inlet 82 to the outlet 84. A portion of the process flow crosses the membrane 66 through the openings 70 in the membrane support 62 (as the permeate or filtrate having the undesired biological products) in a direction 120 perpendicular to direction 118. The number and size of the openings 70 varies between the filtration units 60 of FIGS. 13 and 14 due to the geometry of the features 68. In addition, the surface area of the membrane support 62 adhered to the membrane 66 (via the features 68) is different between the filtration units 60 of FIGS. 13 and 14. As noted above, the adhesion of the features 68 to the membrane 66 minimizes local membrane deflection and, thus, adverse membrane deflection that could occlude flow in the main flow channel (e.g., channel 76).

Figure 15:
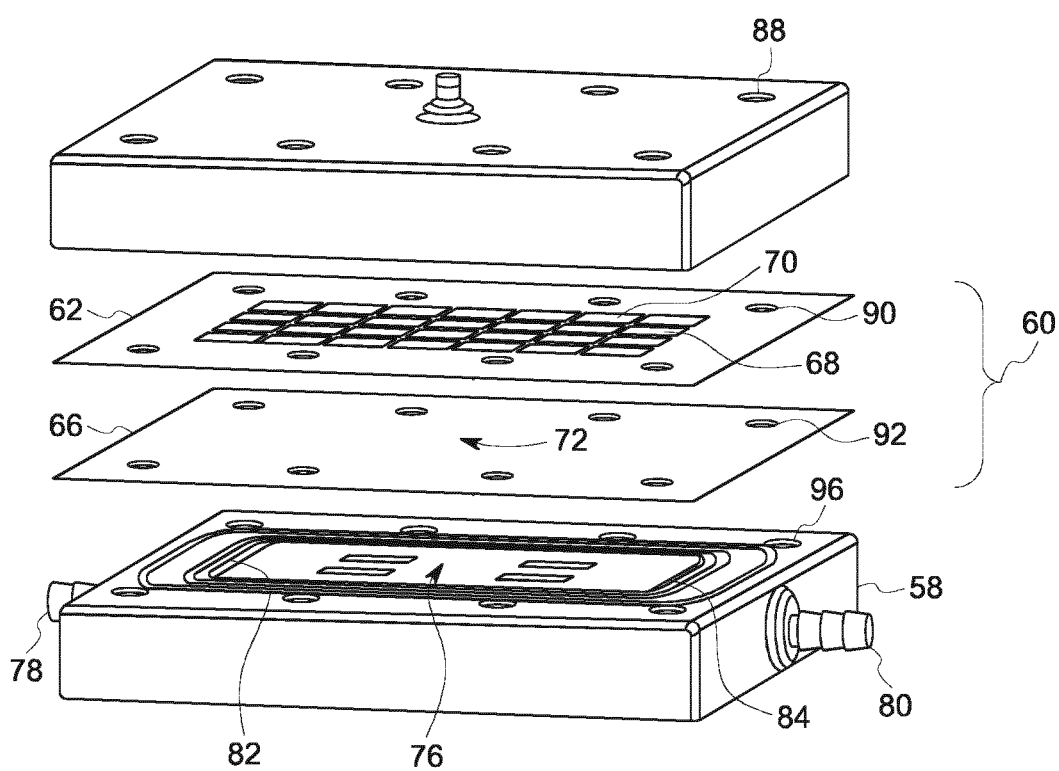
FIG. 15 is an exploded perspective view of an embodiment of a crossflow filtration device (e.g., having no spacer)
Figure 16:
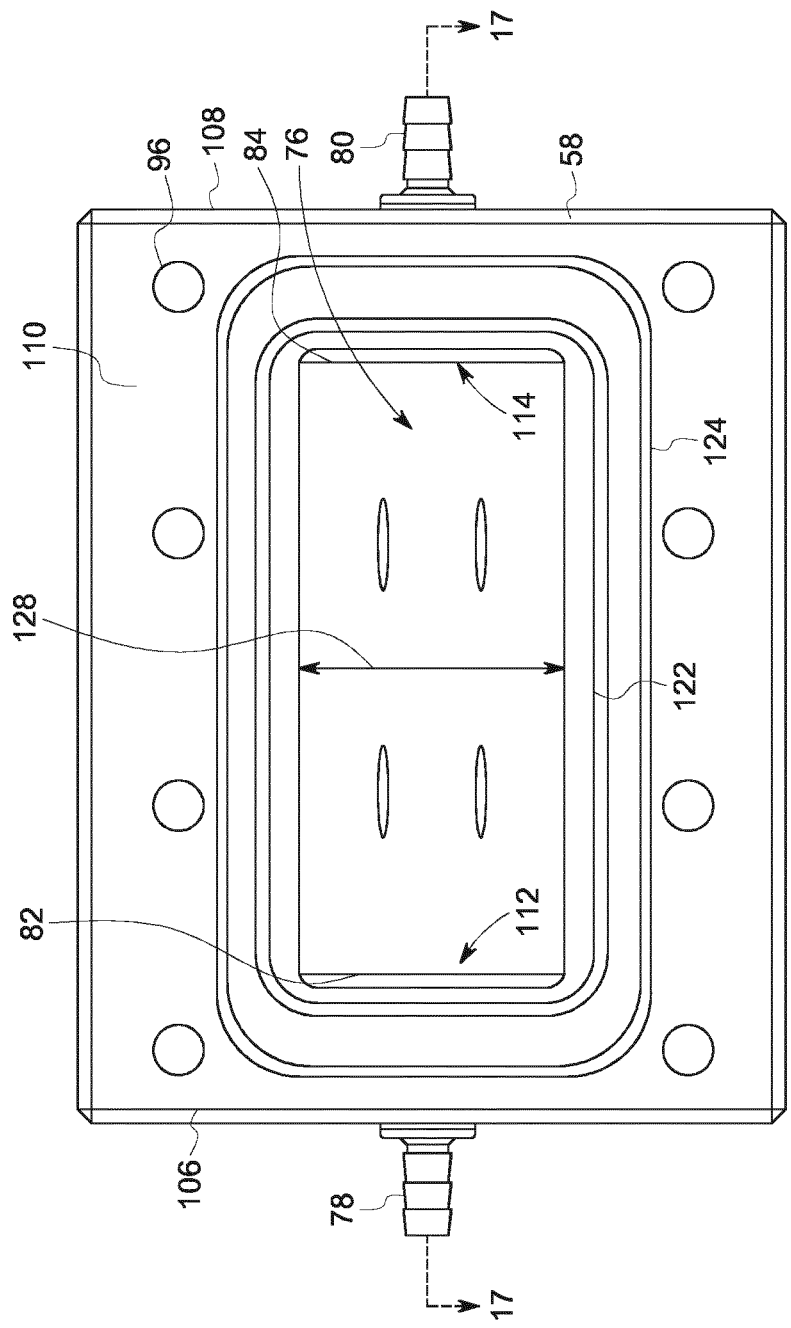
FIG. 16 is a top view of the bottom portion of the crossflow filtration device of FIG. 15.
Figure 17:
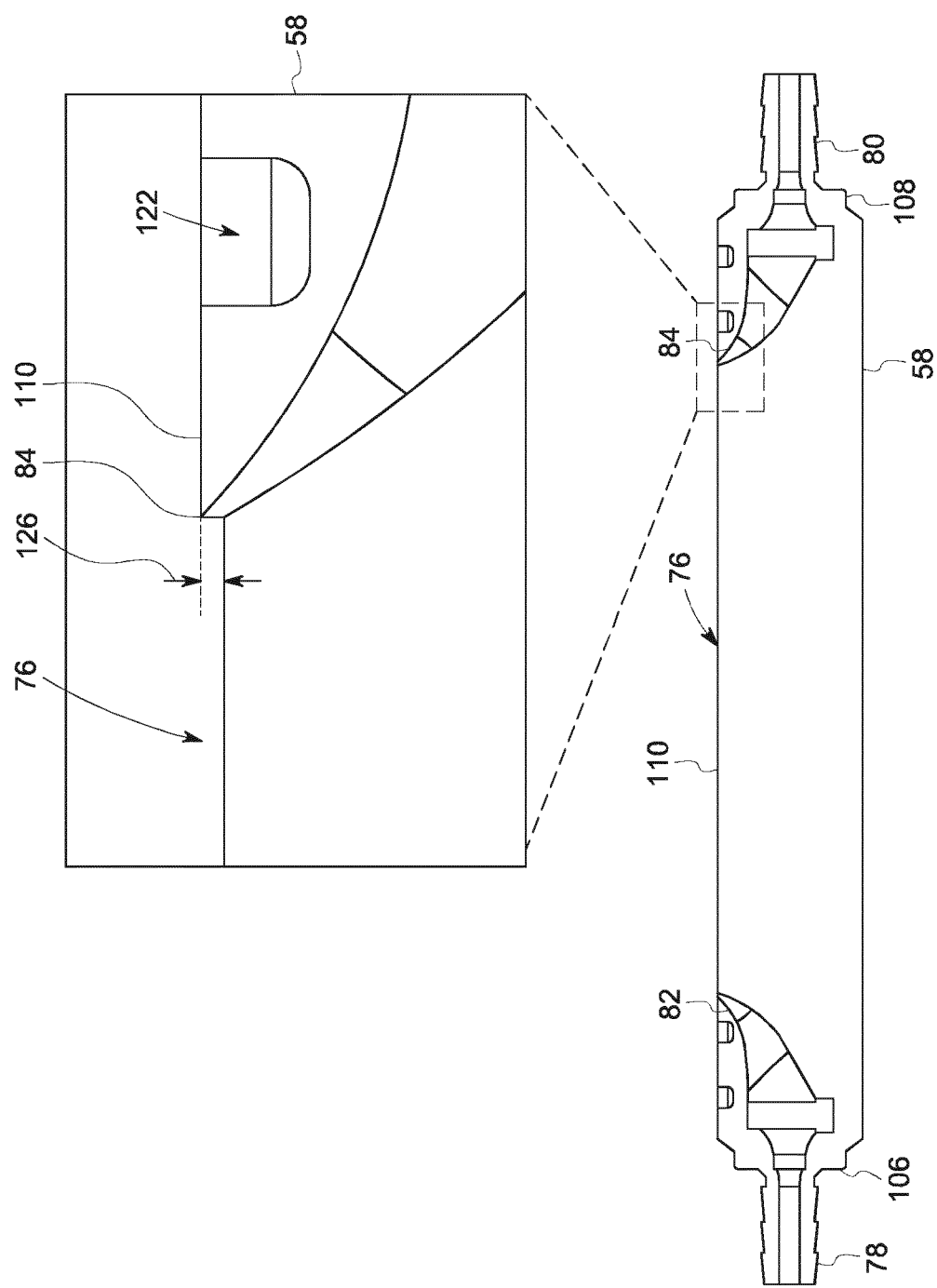
FIG. 17 is a cross-sectional view of the bottom portion of the crossflow filtration device of FIG. 15 taken along line 17-17.

FIG. 15 is an exploded perspective view of another embodiment of the crossflow filtration device 18. FIGS. 16 and 17 are different views of the bottom portion 58. The crossflow filtration device 18 is similar to the device 18 in FIG. 3 except the device 18 has the single channel 76 formed in the bottom portion 58. As a result, the filtration unit 60 does not include a spacer 64. The inlet 82 and the outlet 84 are disposed on the top surface 110 of the bottom portion 58 adjacent opposite longitudinal ends 112, 114 of the channel 76. The port 78 extends to inlet 82 and the outlet 84 extends to port 80. Both ports 78, 80 have a smooth contoured shape to enable a smoother flow of the process flow into and out of the channel 76 with close-to-uniform velocity through and across the width. The single channel 76 is surrounded by concentrically arranged grooves 122, 124 (e.g., O-ring grooves) configured to retain O-rings when the device 18 is assembled to provide a seal. A depth 126 of the channel is dependent on a width 128 of the channel 76 and the flow rate (e.g., of the process volume through the device 18) to achieve the desired shear rate for the process volume passing through the channel 76. The depth 126 may range between approximately 0.25 mm and 0.36 mm. In certain embodiments, a ratio of the channel depth to membrane thickness may be approximately 300 μm/20 μm.

It should be noted as the scale increases for the crossflow filtration device, the design approach does not increase in complexity. For example, to double the processing volume (e.g., from 50 mL to 100 mL) the filtration surface area could be doubled by simply increasing the length and/or width of the membrane. Increasing the length allows for the shear rate to be maintained at the same flow rate, but results in an increase in the overall pressure drop. Increasing the width allows for shear rate to be maintained by increasing the flow rate, while also maintaining the same pressure drop. Due to the membrane support adhering the membrane to the upper or top portion (e.g., via adhesive), scaling to large membrane areas does affect the approach. In addition, the spacers can be utilized to maintain a channel height with better accuracy (and a lower cost) as opposed to relying on tight manufacturing tolerances over a larger/longer area to create a pocket of the correct size.

In addition, the structure of the crossflow filtration device may vary from those described above. For example, in certain embodiments, a thin channel may be sandwiched between a couple membranes. As a result, the filtration device could also have a permeate port at the top surface of the top portion and at the bottom surface of the bottom portion. In certain embodiments, filtration units may be arranged in a serial or parallel manner.

Figure 18:
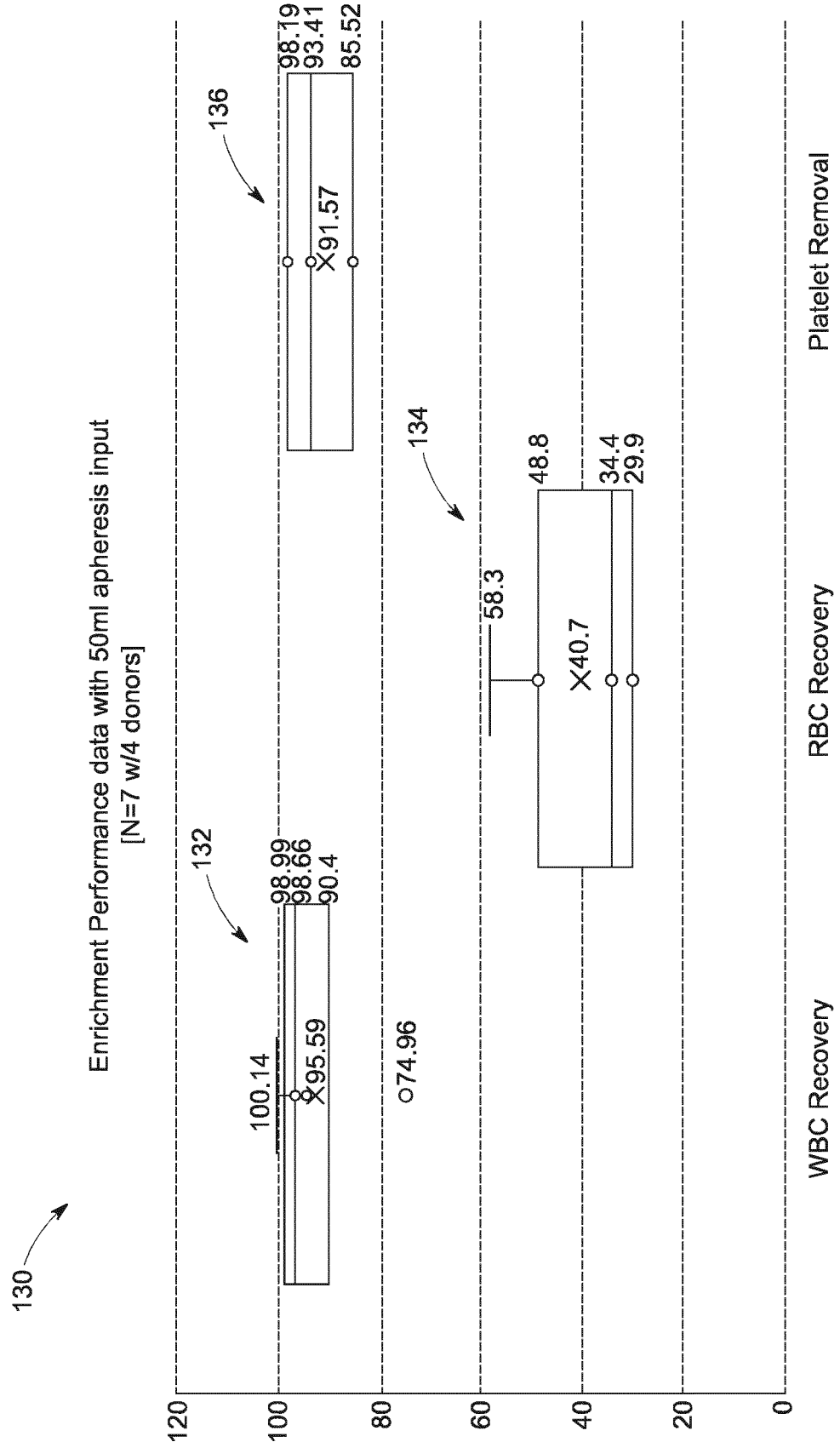
FIG. 18 is a graphical representation of enrichment data utilizing the system of claim 1 for enriching a desired cell population (e.g., monocytes).

FIG. 18 is a graphical representation 130 of enrichment data collected utilizing the system of FIG. 1 for enriching a desired cell population (e.g., lymphocytes). The data in FIG. 18 was collected from 7 apheresis samples collected from 4 different healthy donors. 50 mL volumes were used as the biological sample input in the system 10 described above utilizing the crossflow filtration device 18. Arrow 132 indicates the percentage of white blood cells recovered from the respective samples. Arrow 134 indicates the percentage of red blood cells removed from the respective samples. Arrow 136 indicates the percentage of platelets removed from the respective samples. The graphical representation indicates the system 10 may be effective at enriching lymphocytes from the apheresis samples, while removing most of the platelets and a significant portion of the red blood cells.

Technical effects of the disclosed embodiments include providing an automated enclosed system for enriching a desired cell population from a biological sample (e.g., blood) in a functionally closed system. In addition, a cell enrichment kit is provided that is disposable. Both the costs and the labor associated with cell enrichment are reduced. Further, the cell enrichment kit includes a membrane-based crossflow filtration device. The membrane is part of a laminated filtration unit configured to reduce occlusion of adjacent flow channels within the crossflow filtration device. A larger biological sample can be processed by utilizing a crossflow filtration device loaded with a larger membrane with more effective filtration area to limit the potential for fouling or to reduce processing time or both.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A filtration device for a disposable cell enrichment kit, comprising:
a first mating portion;
a second mating portion;
at least one inlet port;
at least one outlet port; and
a micro-porous membrane disposed between the first and second mating portions, wherein the micro-porous membrane and either the first mating portion or the second mating portion together define at least a portion of a single channel configured to receive a process volume containing a biological sample, and the single channel extends parallel to the micro-porous membrane;
a membrane support disposed between the second mating portion and the micro-porous membrane, the membrane support comprising a first plurality of structural features that define a first plurality of openings, wherein the membrane support is coupled to both the second mating portion and the micro-porous membrane, and the membrane support is coupled to the micro-porous membrane via the first plurality of structural features to provide support; and
a spacer disposed between the micro-porous membrane and the first mating portion, wherein the spacer comprises an opening that further defines a geometry of the single channel,
wherein the micro-porous membrane is laminated between the membrane support and the spacer,
wherein the second mating portion comprises a second plurality of openings defined by a second plurality of structural features,
wherein the second plurality of openings are configured to receive a permeate containing specific biological components that has crossed the micro-porous membrane and through the first plurality of openings of the membrane support for discharge from the filtration device,
wherein the filtration device is configured to retain a specific cell population in a retentate from the process volume and to discharge the retentate from the at least one outlet port, and
wherein the membrane support comprises a plurality of ribs extending across a length and a width of the membrane support, wherein the plurality of ribs define the openings in the membrane support, and wherein the ribs contact the micro-porous membrane.

2. The filtration device of claim 1, wherein the micro-porous membrane has a thickness between 13 and 25 µm, the micro-porous membrane has an effective working area of at least 40 cm², and the single channel has a depth between 0.25 mm and 0.36 mm.

3. The filtration device of claim 1, wherein the single channel is formed in the first mating portion.

4. The filtration device of claim 1, wherein the at least one inlet port and/or the at least one outlet port is configured to provide a substantially uniform velocity of a laminar flow of the process volume across a width of the single channel.

5. A disposable cell enrichment kit, comprising:
a crossflow filtration device configured to be disposed along a main loop pathway and configured to receive a process volume containing a biological sample and to utilize crossflow filtration, via a micro-porous membrane, to retain a specific cell population in a retentate from the process volume and to remove a permeate including specific biological components from the process volume, wherein the crossflow filtration device comprises a first mating portion, a second mating portion, and a laminated filtration unit, the laminated filtration unit comprising:
the micro-porous membrane;
a membrane support comprising a first plurality of structural features that define a first plurality of openings, wherein the first plurality of structural features are coupled to and provide support to the micro-porous membrane, and the first plurality of openings allow the permeate to flow through them after crossing the micro-porous membrane; and
a spacer comprising an opening that defines at least a portion of a geometry of the at least one channel,
wherein the spacer is disposed between the micro-porous membrane and the first mating portion,
wherein the membrane support is configured to be disposed between the micro-porous membrane and either the first mating portion or the second mating portion, and
wherein the first plurality of structural features of the membrane support comprises a plurality of ribs extending across a length and a width of the membrane support, wherein the plurality of ribs define the first plurality of openings in the membrane support.

6. The disposable cell enrichment kit of claim 5, wherein the second mating portion comprises a second plurality of openings defined by a second plurality of structural features, wherein the second plurality of openings are configured to receive the permeate that has crossed the micro-porous membrane and through the first plurality of openings of the membrane support for discharge from the crossflow filtration device.

7. The disposable cell enrichment kit of claim 5, wherein first mating portion and the micro-porous membrane define at least a portion of at least one channel within the crossflow filtration device configured to receive the process volume containing the biological sample.

8. The disposable cell enrichment kit of claim 7, wherein the crossflow filtration device comprises at least one inlet port configured to receive the process volume and at least one outlet port to discharge the retentate, and the single inlet port and the single outlet port are fluidly coupled to the at least one channel.

9. The disposable cell enrichment kit of claim 8, wherein the at least one channel is formed in the first mating portion.

10. The disposable cell enrichment kit of claim 5, comprising a process vessel disposed along the main loop pathway downstream of the crossflow filtration device and configured to receive the process volume following crossflow filtration.

11. The disposable cell enrichment kit of claim 10, comprising a buffer vessel disposed along a buffer pathway coupled to the main loop pathway and configured to provide a buffer to the process volume to supplement the process volume.

12. The disposable cell enrichment kit of claim 10, wherein the process vessel comprises an inlet to receive the process volume following crossflow filtration, via the crossflow filtration device, and an outlet to discharge the process volume from the process vessel and the process vessel tapers from the outlet to the inlet.

13. The disposable cell enrichment kit of claim 10, comprising a source vessel coupled to a source pathway coupled to the main loop pathway, wherein the source vessel is configured to receive the biological sample and to provide it to the main loop pathway, via the source pathway at a location along the main loop pathway.

14. The disposable cell enrichment kit of claim 13, comprising a waste vessel coupled to a waste pathway coupled to the crossflow filtration device, wherein the waste vessel is configured to receive the permeate from the crossflow filtration device via the waste pathway.

* * * * *